United States Patent [19]

Wenshau et al.

[11] Patent Number: 5,154,087
[45] Date of Patent: Oct. 13, 1992

[54] SAMPLER APPARATUS

[75] Inventors: Hugo Wenshau, Dallas; Grant G. Rice, Arlington, both of Tex.

[73] Assignee: Intersystems, Inc., Omaha, Nebr.

[21] Appl. No.: 471,555

[22] Filed: Jan. 29, 1990

[51] Int. Cl.⁵ .......................... G01N 1/20; G01N 1/08
[52] U.S. Cl. ............... 73/863.85; 73/864.43; 73/863.81
[58] Field of Search .......... 73/863.85, 863.81, 863.51, 73/863.52, 863.53, 863.54, 863.01, 864.43, 863.82, 863.83, 863.84, 863.86, 863.56

[56] References Cited

U.S. PATENT DOCUMENTS

| 2,370,260 | 2/1945 | Robison | 73/863.54 |
| 3,241,371 | 3/1966 | Horeth | 73/863.83 X |
| 3,348,419 | 10/1961 | Addison | 73/863.83 |
| 3,383,924 | 5/1968 | Cordell | 73/863.83 |
| 3,472,079 | 10/1969 | Cordell | 73/863.51 X |
| 3,822,600 | 7/1974 | Stonner et al. | 73/864.43 |
| 4,149,414 | 4/1979 | Walker | 73/864.43 |
| 4,433,587 | 2/1984 | Risdal | 73/863.83 X |
| 4,479,393 | 10/1984 | Shores | 73/863.86 X |

FOREIGN PATENT DOCUMENTS

| 388213 | 10/1973 | U.S.S.R. | 73/863.83 |
| 684823 | 12/1952 | United Kingdom | 73/863.81 |

Primary Examiner—Tom Noland
Attorney, Agent, or Firm—Bernard Malina

[57] ABSTRACT

A sampler apparatus includes a housing which is adapted for mounting on pressurized conveying lines and a remotely mounted control unit. The housing includes a sampling probe which is extended from the housing to enter the conveying line and collect a sample of material flowing in the conveying line and then is retracted into the housing. An auger is provided to clean out the sampling probe when in the retracted position and force the sampled materials into a discharge tube. The control unit controls the timing of the extension and the retraction portion of the operating cycle.

14 Claims, 3 Drawing Sheets

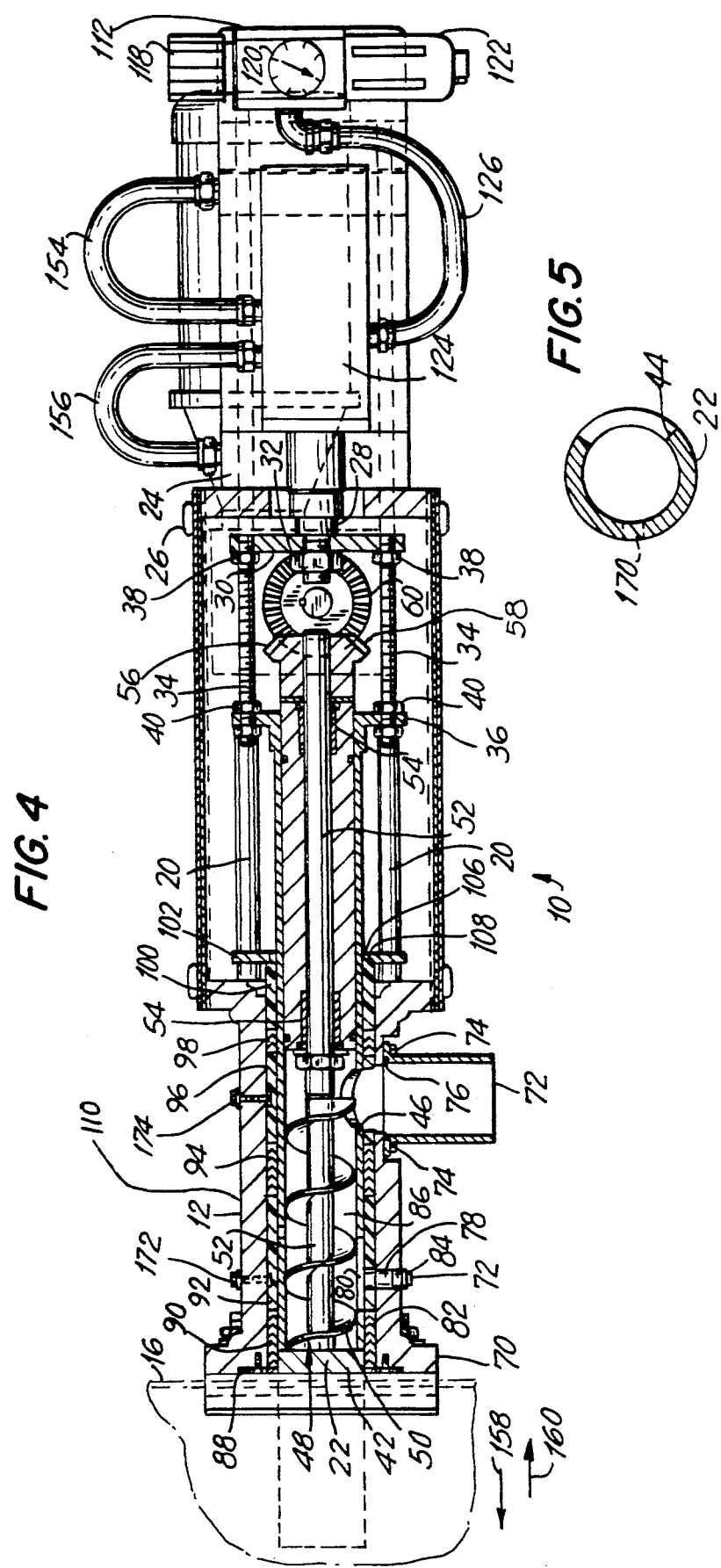

SAMPLER APPARATUS

BACKGROUND OF THE INVENTION

In the process of manufacturing various products such as paper and cardboard, pulp is produced as an intermediate product. The pulp is produced from wood chips which are sized and screened for removal of unwanted materials and then fed into a digester apparatus. In the digester apparatus, the temperature and pressure are raised to levels in the order of 300° F. and 150 psig, causing the lignin in the wood to be removed. The remaining product, which is called pulp, is a generally brown or greyish slurry which has the general consistency of wet tissue paper. The pulp is removed from the digester by pressure pumps which transport the pulp from the digester to a storage tank.

The consistency and strength of the fibers in the newly manufactured pulp is an important factor in determining the quality of the finished paper or cardboard product and a means for extracting a representative sample of the pulp is required in order to perform the appropriate quality control tests.

In the past, various types of apparatus have been used in an attempt to remove representative samples of the pulp as it is transferred from the digester. The most common technique for pulp sampling includes the use of a valve which is attached to the conveying line. The valve is opened allowing some of the pulp in the conveying line to flow through the valve into a suitable container. This technique results in numerous operational problems, most of which are due to the plugging of the valve and the ports due to the high concentration of fibers and other materials in the pulp.

Another technique for pulp sampling is called the "block and bleed" system. In this technique, the pulp is allowed to flow into a by-pass pipe line which is blocked by a strainer. The fiberous material in the pulp is strained and the liquid is allowed to continue on and rejoin the flow in the conveying system. The system is operated by a series of valves which are opened and closed in order to extract a pulp sample.

This system, like the previous system, must be operated manually, resulting in high operation costs and high maintenance costs. These systems also must be operated under conditions of high temperature and high pressure resulting in safety problems associated with manual operation.

The prior art related to sampling devices includes U.S. Pat. No. 3,383,924 issued to Ray R. Cordell, which includes a retractable sampling tube and an auger mounted in the sampling tube for cleanout of the sampling tube after each sampling operation. This device is particularly adapted for the sampling of finely granulated materials in pressurized conveyor lines, however it is not suitable for the sampling of slurries such as paper pulp which includes large particles of bark or other solid materials.

OBJECTS OF THE INVENTION

It is an object of the invention to provide a sampler which is capable of extracting samples of various types of solids and slurries including paper pulp under conditions of high temperature and high pressure.

Another object of the present invention is to provide a sampler capable of operation under pressures of approximately 150 psig and temperatures of approximately 300° F.

Another object of the present invention is to provide a sampler which can be easily installed on existing paper making equipment.

Another object of the present invention is to provide a sampler which automatically extracts a sample of pulp without the need for manual operation or intervention.

Another object of the present invention is to provide a sampler which operates in a reliable and safe manner.

Another object of the present invention is to provide a sampler which is capable of extracting pulp samples without halting or interfering with the normal flow of materials through a pulp and paper mill.

Another object of the present invention is to provide a sampler which is capable of extracting either a single sample or a composite sample consisting of a plurality of individual samples collected during various time intervals.

Another object of the present invention is to provide a sampler which is capable of extracting and collecting and storing sampled materials in a sealed container, thus enabling the sampling of dangerous materials in a safe and effective manner.

Still another object of the present invention is to provide a sampler which is composed of a relatively small number of component parts which are simple to manufacture, resulting in a relatively low overall cost.

SUMMARY OF THE INVENTION

In accordance with the present invention, there is provided a sampler apparatus which is mounted on a pulp conveying line using a flange mounted arrangement. The apparatus includes a sampling probe which is extended into the conveying line during the sampling process. The sampling probe is mounted on a housing which includes a motor and driving connections for extension of the sampling probe into the conveying line, retraction of the sampling probe into the housing and operation of an auger which is mounted in the sampling probe. When the sampling probe is completely retracted into the housing operation the auger forces pulp and liquid collected by the sampling tube from the conveying line to be discharged through a discharge port. The discharged material then falls by gravity into a discharge pipe and then into a sealed storage or collection container.

The sampling probe extends across the full width of the conveying line, thereby ensuring that a representative sample of the material in the conveying line is collected. The sample probe is at the same pressure as the conveying line when it is inserted, thereby further ensuring that there is no classification or stratification of the product. The housing includes pressure seals which prevent blow-by or escape of the high pressure pulp flowing in the conveyor line.

BRIEF DESCRIPTION OF THE DRAWINGS

Additional objects and a further understanding of the invention may be had by referring to the following specification and drawings in which:

FIG. 4 is a cross-sectional view taken along the line 4—4 of FIG. 2; and

FIG. 5 is a cross-sectional view taken along the line 5—5 of FIG. 3.

DETAILED DESCRIPTION OF THE INVENTION

Figure 1:
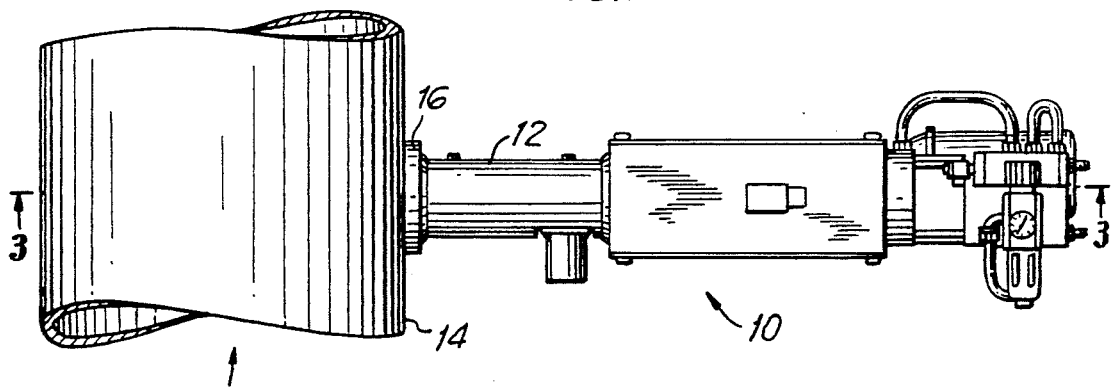
FIG. 1 is a side elevation view of a pulp sampler apparatus in accordance with the present invention, with the apparatus shown in use attached to a conveying line.
Figure 2:
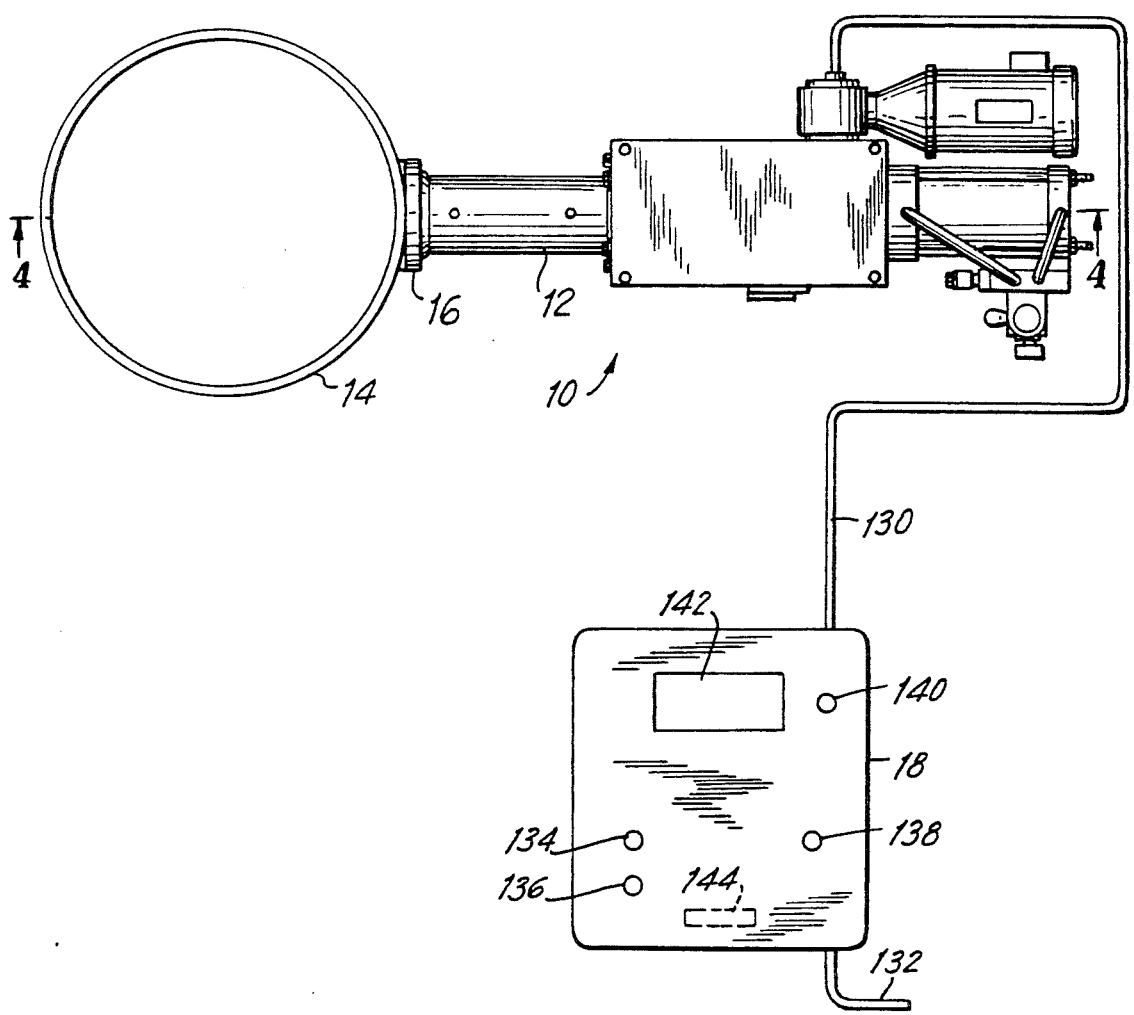
FIG. 2 is a plan view of the pulp sampler apparatus of FIG. 1.
Figure 3:
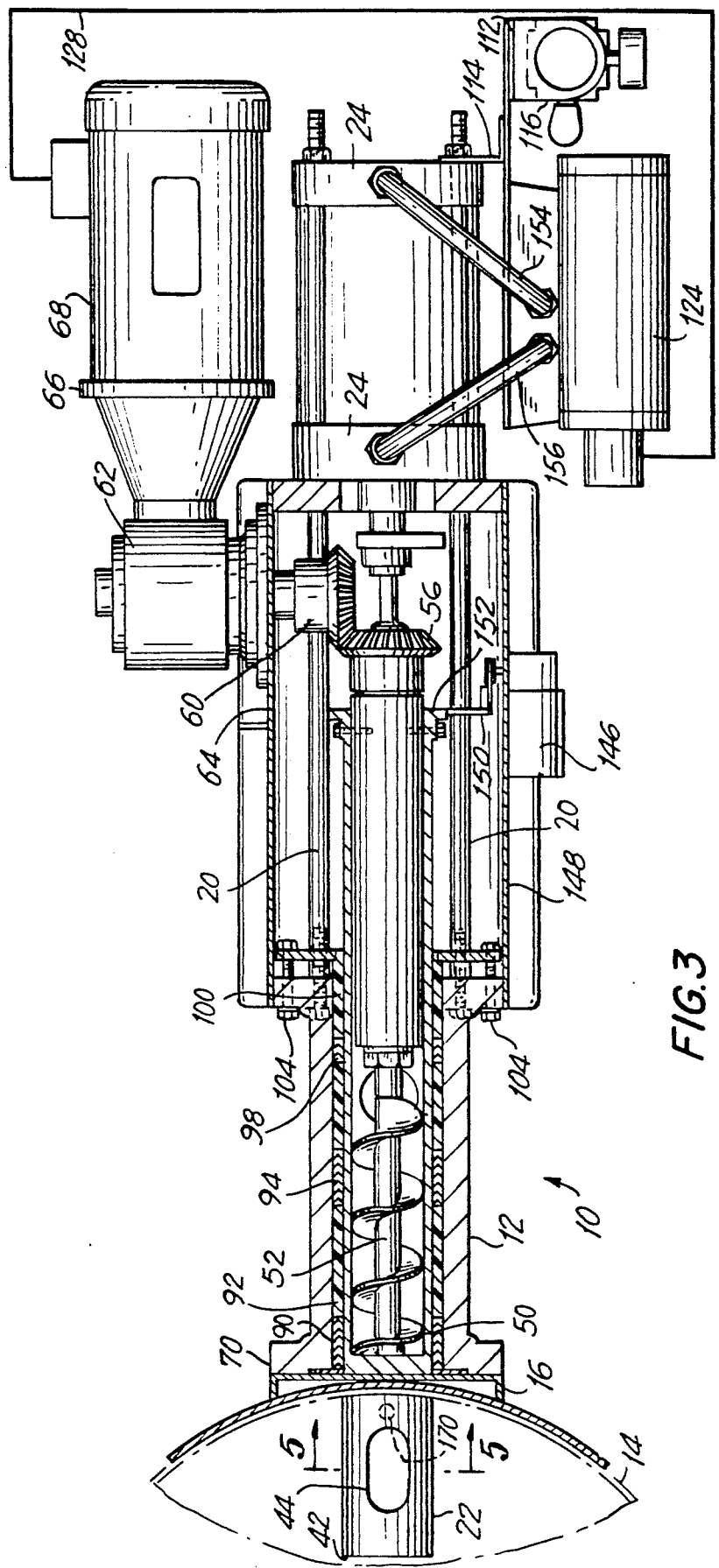
FIG. 3 is a cross-sectional view taken along the line 3—3 of FIG. 1.

With reference to the drawings, there is shown in FIGS. 1 and 2 an overall view of a sampler apparatus made in accordance with the present invention which is generally denoted by the reference numeral 10. The apparatus includes a housing 12 which is shown in use, mounted on a pulp conveyor line 14 by means of a mount 16 which is welded on the conveyor line 14 and a control unit 18 which may be mounted remotely.

Within the housing 12 there are a pair of guide rods 20 which support a sampling probe 22 which may be extended from the housing 12 in order to project into the conveyor line 14 and thereby obtain a sample of the pulp or other materials flowing in the conveyor line 14. The extension and retraction of the sampling probe 22 relative to the housing 12 is controlled by means of an air cylinder 24 which is mounted on the rear surface 26 of the housing 12. The air cylinder 24 includes an actuator shaft 28 which is connected to a guide plate 30 by means of a nut 32. The guide plate 30 is connected to a pair of threaded adjustment rods 34 which are, in turn, connected to a flange 36 formed on the sampling probe 22.

The position of the sampling probe 22 relative to the actuator shaft 28 may be adjusted by means of the threaded adjustment rods 34. Once the adjustment has been made, it may be locked using nuts 38 which bear against the guide plate 30 and nuts 40 which bear against the flange 36.

The sampling probe 22 has the overall configuration of a hollow cylinder having a closed end 42. The sampling probe 22 includes a sample inlet port 44, a discharge port 46, and a bleed hole 170, the operation of which will be described presently.

Mounted within the sampling probe 22 there is an auger assembly 48 which includes an auger blade 50 mounted on an auger shaft 52 which is rotatably mounted in auger shaft bearings 54 for rotation relative to the sample probe 22. A miter gear 56 is mounted on the end 58 of the auger shaft 52 and when the sampling probe 22 is in the retracted position shown in FIG. 4, the miter gear 56 is in mesh with a miter gear 60 which is connected to a speed reducer 62. The speed reducer 62 has a preferred speed reduction ratio in the order of thirty to one and is mounted on the outer surface 64 of the housing 12. The speed reducer 62 has a right angle configuration and includes a mounting flange 66 for an electric motor 68 which is mounted in a configuration which is parallel to the housing 12, thereby reducing the space needed for the installation of the apparatus 10 and reducing the eccentric loading on the mounting flange 70 of the housing 12.

When the miter gears 56, 60 are in mesh, the electric motor 68 rotates the auger shaft 52 enabling the auger blade 50 to bring sample materials, which have entered the sampling probe 22 via the sample inlet port 44, to the discharge port 46, whereupon the sample materials flow into a discharge tube 72 which is mounted on the housing 12. The sample materials flow through the discharge tube 72 under the influence of gravity for collection by conventional means, thereby enabling the performance of various quality control tests and measurements on the sample materials.

The bleed hole 170 is spaced about 180° from the sample inlet port 44 close to the wall of conveyor line 14 and enables materials to enter the sampling probe 22 easily without the possibility of creating an unwanted air pocket which would impede the flow of materials into the sampling probe 22.

The discharge tube 72 is attached to the housing 12 by means of bolts 74 and an 0-ring seal 76 prevents sample materials from leaking between the housing 12 and the discharge tube 72.

The discharge tube 72 may be connected to a sealed container which is not illustrated. This sealed container facilitates the collection of materials which may be hot, corrosive or otherwise dangerous in a safe and effective manner.

The housing 12 includes a purge fitting 78 which is in line with and communicates with a purge port 80 formed in a forward portion 82 of the sampling probe 22. The purge fitting 78 includes a threaded plug 84 which may be removed during use and the purge fitting 78 may be connected to a source of cleaning fluid using conventional conduit means. The purge fitting 78 may thus be used to purge or wash down the interior portion 86 of the sampling probe 22 and the auger assembly 48 in-between sampling cycles. The incorporation of this wash-down capability represents an optional feature or alternative embodiment of the present invention which may be used, as desired, to augment the sampling capability of the apparatus 10.

One potential application of this wash-down capability is the wash-down of the apparatus 10 in-between use of the apparatus 10 to sample different materials flowing in the conveyor line 14, thereby ensuring the accuracy of the sample and preventing contamination of a sample with materials sampled during a previous cycle.

The apparatus 10 according to the present invention incorporates a plurality of seals which are disposed to seal against unwanted leakage of materials flowing under pressure in the conveyor line 14 through the various apertures and interfaces of the apparatus 10. The mounting flange 70 of the housing 12 includes an O-ring seal 88 which prevents leaking between the mounting flange 70 and the mount 16.

Mounted between the sample probe 22 and the housing 12 there is a first plurality of packing rings 90, a front seal spacer 92, a second plurality of packing rings 94, a middle seal spacer 96, a third plurality of packing rings 98, and a rear seal spacer 100. A packing compression plate 102 is connected to the housing 12 by means of screws 104 and bears against the rear seal spacer 100, thereby compressing the first 90, second 94, and third plurality of packing rings 98.

The seal spacers 92, 96, 100 are preferably made of Nylon or a similar material. The packing rings 90, 94, 98 are preferably made of Teflon or a similar material and the packing rings 90, 94, 98 have a generally V-shaped configuration.

Bolts 172 and 174 prevent seal spacers 92 and 96 from rotating.

The rear spacer 100 has a stepped portion 106 which projects into the aperture 108 of the compression plate 110 and thereby prevents the compression plate 110 from contacting the sampling probe 22.

The combination of the compression plate 110, seal spacers 92, 96, 100 and packing rings 90, 94, 98 seal the apparatus 10 against unwanted leakage of material flowing in the conveying line 14 while facilitating reciprocating motion of the sampling probe 22 which is driven by the air cylinder 24.

The O-ring seals 76, 88 are preferably made of Neoprene for increased thermal and pressure resistance.

The air cylinder 24 is operated by a source of high pressure air which flows into and is controlled by a filter regulator 112 which is mounted on the housing 12 by means of a bracket 114. The filter regulator 112 includes an air inlet port 116, a pressure adjustment control knob 118, a pressure gage 120, and a filter 122.

The motion of the actuator shaft 28 is controlled by a two-position solenoid valve 124 which is mounted on the bracket 114. The solenoid valve 124 is connected to the air cylinder 24 via compressed air lines 154, 156 and to the filter regulator 112 via a compressed air line 126 and is connected to the motor 68 via an electrical line 128. The motor 68 is connected to the control unit 18 via an electrical line 130 and the control unit 18 is connected to a source of electrical power via an electrical line 132.

The control unit 18 includes an on/off switch 134, a manual sampling or manual operation switch 136, a manual-automatic operation selector switch 138, a sampling indicator 140, and an adjustable timer or counter 142. The on/off switch 134 controls the electrical power input to the control unit 18. When electrical power is on and the manual-automatic operation selector switch 138 is in the automatic operation mode, the time cycle on the digital timer 142 is displayed. The manual-automatic operation selector switch 138 allows an operator to receive a sample on an automatically timed interval or receive an instant or single sample when this switch 138 is used in conjunction with the manual sampling switch 136. The manual sampling switch 136 will function when the manual-automatic operator selector switch 138 is in the manual mode. Actuation of this switch 138 causes the apparatus 10 to operate through a single cycle and obtain a single sample. The sampling indicator 140 is illuminated when the solenoid valve 124 is actuated or the motor 68 is in operation. The adjustable timer 142 enables an operator to select the time interval between the end of a sampling cycle and the start of the next sampling cycle.

An adjustable solenoid timer 144 is mounted internally within the control unit 18 and is shown in broken lines in FIG. 2. The adjustable solenoid timer 144 is used to control the length of time that the sampling probe 22 is extended into the product stream.

A motor limit switch 146 is mounted on the outer surface 148 of the housing 12 and includes an arm 150 which is activated by the flange 152. This switch 146 assures that the sample tube 22 has been completely withdrawn from the conveyor line 14 and that the miter gears 56, 60 are properly meshed before the motor 68 is activated.

During operation of the apparatus 10, the sample probe 22 is driven into and out of the conveyor line 14 in the directions shown by the arrows 158, 160 in FIG. 4 by the pneumatic air cylinder 24. The air cylinder 24 operates under the control of the solenoid valve 124. The solenoid valve 124 is conventional in nature and includes an internal spool, a solenoid and a return spring. These components are well known in the art and have, therefore, not been illustrated. When the solenoid is energized, the internal spool directs compressed air through the compressed air line 154, causing the air cylinder to extend the sampling probe 22. When the solenoid is de-energized, the return spring returns the internal spool to a normal position and the internal spool directs compressed air through the compressed air line 156, causing the air cylinder to retract the sampling probe 22.

Retraction of the sampling probe 22 causes the flange 152 to actuate the limit switch 146 which starts the operation of the motor 68 to drive the auger assembly 48. The control unit 20 imposes a relatively short time delay prior to the start of the motor 68 to ensure that the sampling probe 22 has been completely retracted and the gears 56, 60 are properly in mesh. This time delay is preferably in the order of one and one-half seconds. After the motor 68 has run for a preselected amount of time, which is in the order of 25 seconds, the motor 68 is shut off and the timer 142 is energized and operates for a selected period and then starts a new sampling cycle.

The apparatus according to the present invention may be mounted in a horizontal position as shown in FIG. 1 where the material flow in the conveyor line 14 is vertically up or down, or alternatively may be mounted in an inclined position where the conveyor line is positioned angularly. It is understood that in whatever orientation, the sample inlet part 44 will face the material flow.

In alternative embodiments of the invention which are not shown, the drive apparatus for driving the sampling probe 22 may be all electric, pneumatic or hydraulic or a combination thereof.

While preferred embodiments of the invention have been shown and described herein, it is obvious that numerous changes and omissions may be made in such embodiments without departing from the spirit and scope of the invention.

What is claimed is:

1. A sampler apparatus for sampling materials in a pressurized conveyor line comprising
   a housing,
   attachment means for attaching said housing to said pressurized conveyor line,
   hollow sampling probe means mounted in said housing, with said sampling probe capable of translation to an extended position relative to said housing and a retracted position, with said sampling probe when in said extended position projecting into said pressurized conveyor line, and with said sampling probe when in said retracted position retracted into said housing, with said sampling probe means including an inlet aperture and a discharge aperture,
   probe drive means for reversibly driving said sampling probe from said retracted position to said extended position,
   auger means mounted in said sampling probe, means for cleaning said auger means when said sampling probes means is in said retracted position,
   auger drive means mounted on said housing for driving said auger drive means, and control means for controlling the operation of said probe drive means and said auger drive means, said housing including a purge port and said sampling probe including a purge aperture and with said purge port and said purge aperture substantially in alignment when said sampling probe is in said retracted position.

2. A sampler apparatus according to claim 1 in which said probe drive means comprises a pneumatic actuator.

3. A sampler apparatus according to claim 1 in which said auger drive means comprises an electric motor.

4. A sampler apparatus according to claim 3 in which said auger drive means further comprises a right-angle speed reducer.

5. A sampler apparatus according to claim 1 in which said control means includes timer control means for controlling the length of time said sampling probe is in said extended position and in said retracted position.

6. A sampler apparatus according to claim 1 in which said control means includes manual control means for manual operation of said apparatus and automatic control means for automatic operation of said apparatus and switch means for selection of manual or automatic operation with said manual control means comprising a control button for controlling extension and retraction of said sampling probe.

7. A sampler apparatus according to claim 1 in which said housing further comprises a discharge tube with said discharge tube substantially in alignment with said discharge aperture when said sampling probe is in said retracted position.

8. A sampler apparatus according to claim 1 in which said control means includes timer control means for controlling the length of time said sampling probe is in said retracted position.

9. A sampler apparatus according to claim 1 in which said control means includes solenoid valve means.

10. A sampler according to claim 1 in which said control means includes limit switch means.

11. A sampler according to claim 1 further comprising sampler seal means disposed between said sampling probe means and said housing.

12. A sampler according to claim 11 in which said sampler probe seal means comprises a plurality of packing rings.

13. A sampler according to claim 11 further comprising compression means for compression of said packing rings.

14. A sampler according to claim 1 in which said attachment means for attaching said housing to said pressurized conveyor line further comprises housing seal means for sealing against leakage of said materials flowing in said pressurized conveyor line.

* * * * *